(12) United States Patent
Janik et al.

(10) Patent No.: US 7,075,073 B1
(45) Date of Patent: Jul. 11, 2006

(54) ANGLE RESOLVED X-RAY DETECTION

(75) Inventors: Gary R. Janik, Palo Alto, CA (US);
Jeffrey A. Moore, San Jose, CA (US);
Edward M. James, San Francisco, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 146 days.

(21) Appl. No.: 10/851,437

(22) Filed: May 21, 2004

(51) Int. Cl.
*G21K 1/02* (2006.01)

(52) U.S. Cl. .................. 250/310; 250/306; 250/505.1; 378/70; 378/72; 378/147

(58) Field of Classification Search ................ 250/310, 250/306, 307, 505.1; 378/70, 71, 72, 84, 378/85, 145, 147
See application file for complete search history.

(56) References Cited

U.S. PATENT DOCUMENTS

| | | | | |
|---|---|---|---|---|
| 3,562,525 A | * | 2/1971 | Constantine et al. | 378/48 |
| 4,467,199 A | * | 8/1984 | Sato | 250/310 |
| 5,481,109 A | * | 1/1996 | Ninomiya et al. | 250/310 |
| 5,497,008 A | * | 3/1996 | Kumakhov | 250/505.1 |
| 5,569,919 A | * | 10/1996 | Yokoyama et al. | 250/309 |
| 5,682,415 A | | 10/1997 | O'Hara | 378/147 |
| 5,926,522 A | * | 7/1999 | McCarthy et al. | 378/84 |
| 6,271,534 B1 | * | 8/2001 | Kumakhov | 250/505.1 |
| 6,407,386 B1 | | 6/2002 | Dotan et al. | |

FOREIGN PATENT DOCUMENTS

FR WO 03/083892 9/2003

OTHER PUBLICATIONS

U.S. Appl. No. 09/695,726, filed Oct. 23, 2000, Lee.
U.S. Appl. No. 10/317,607, filed Dec. 11, 2002, Janik et al.
U.S. Appl. No. 10/796,577, filed Mar. 8, 2004, Testoni.
Wilkinson et al., *Nondestructive Angle-resolved X-ray Depth Profiling*, Microsc. Microanal. 6, 517-531, Microscopy Society of America, 2000.
Serulnik, "Defect Topographic Maps Using a Non-Lambertian Photometric Stereo Method", Applied Materials, Israel Ltd., Jul. 2002.

* cited by examiner

*Primary Examiner*—Kiet T. Nguyen
(74) *Attorney, Agent, or Firm*—Luedeka, Neely & Graham, P.C.

(57) ABSTRACT

An apparatus for detecting properties of a sample. An electron beam generator produces an electron beam and directs the electron beam at a desired point on the sample. The sample thereby emits characteristic x-rays at takeoff angles. A collimator receives and parallelizes the x-rays and converts the takeoff angles of the x-rays to positional differences between the parallelized x-rays. A diffractor receives and deflects the x-rays. A position sensitive detector receives the deflected x-rays and detects the positional differences between the x-rays, and generates signals that are characteristic of the received x-rays. An analyzer receives the signals from the detector and determines the properties of the sample based at least in part on the positional differences between the x-rays.

20 Claims, 5 Drawing Sheets

ANGLE RESOLVED X-RAY DETECTION

FIELD

This invention relates to the field of integrated circuit fabrication. More particularly, this invention relates to analyzing the properties, such as thickness and composition, of a sample, such as layers used to form integrated circuits on a semiconducting substrate.

BACKGROUND

Integrated circuit fabrication is typically accomplished by forming many different layers on a substrate. As used herein, the phrase integrated circuit refers to circuits such as those formed on monolithic substrates of a semiconducting material, such as group IV materials like silicon and germanium, and group III–V compounds such as gallium arsenide. Because the design tolerances of an integrated circuit are so strict, it is desirable to monitor the properties, such as thickness and elemental composition, of the various layers as they are formed. One way to measure the properties of film layers is to use electron microprobe x-ray spectrometry.

Electron microprobe x-ray spectrometry uses an electron beam source to excite a sample. X-rays having wavelengths that are characteristic of the elements of the sample are emitted from the sample over a continuous range of takeoff angles, defined as the angle between the x-ray and the sample surface. An x-ray detector assembly is positioned to detect a fraction of the x-rays that are emitted from the sample. The detector assembly can capture x-rays emitted over a finite range of takeoff angles. The detector assembly includes both a spectrometer and an x-ray detector. The spectrometer selects x-rays within a narrow range of wavelengths and directs only those x-rays to the x-ray detector. This is typically accomplished by rotating a diffractor through a range of angles, where at each angular position of the diffractor, the diffractor deflects x-rays with a given wavelength range towards the detector. The rate of impingement of the x-rays within subsets of the desired range of wavelengths is sequentially detected and measured. From this information, properties such as the elemental composition and thickness of the sample can eventually be determined.

The x-ray detector assembly collects x-rays over a finite range of takeoff angles and counts them as an aggregated unit. For a given electron beam energy, data collected from each element in the sample consists of a single number, the x-ray counts per second within the characteristic wavelength range for that element. Since there are usually only two or three elements present, the entire data set likewise consists of only two or three numbers. This is just barely a sufficient amount of data to determine the thickness and the composition of the sample, as there are typically many different variables that are confounded within this data. There is no redundancy in the data that can be used to check for inconsistencies or departures from the mathematical model that is used to analyze the data. Additional data can be obtained by changing the electron beam energy and counting the x-rays again, but this is time consuming and requires more complex electron optics and control electronics.

Because electron microprobe x-ray spectrometry can provide information in a nondestructive manner, it would appear that x-ray spectrometry would be an excellent tool for use in the integrated circuit fabrication industry. Unfortunately, electron microprobe x-ray spectrometry tends to be too slow for use as an in-process tool because of the slow scanning process that must be performed, as introduced above. Not only must a spectrometer be scanned through the desire range of wavelengths, but each scan position must be held for a given length of time so that a sufficient amount of x-rays can be collected to give a valid reading. Further, if the energy of the sample excitation is changed to produce additional, confirmatory information, then the entire scanning process must be performed again as many times as necessary. This tends to make electron microprobe x-ray spectrometry too time consuming for use as an in-process measurement tool.

What is needed, therefore, is an x-ray spectrometer that overcomes some of the problems described above.

SUMMARY

The above and other needs are met by an apparatus for detecting properties of a sample. An electron beam generator produces an electron beam and directs the electron beam at a desired point on the sample. The sample thereby emits characteristic x-rays over a full hemispheric range of takeoff angles, which is defined herein as being from zero degrees to ninety degrees from the plane of the sample. A diffractor receives and deflects to a detector only those x-rays within a desired range of wavelengths, while converting the takeoff angles of the deflected x-rays to positional differences between the deflected x-rays. A position sensitive detector receives the deflected x-rays and detects the positional differences between the x-rays, and generates signals that are characteristic of the received x-rays. An analyzer receives the signals from the detector and determines the properties of the sample based at least in part on the positional differences between the x-rays.

In this manner, the apparatus of the present invention provides a relatively greater amount of information in regard to the sample in a relatively shorter period of time, because more information in regard to the sample is gathered by the apparatus simultaneously. Specifically, the takeoff angles of the x-rays from the sample, which takeoff angles contain additional information about the sample, are preserved in positional differences between the x-rays. Because the detector is able to determine the positional differences between the x-rays, the information contained in the various takeoff angles of the x-rays is preserved and not discarded, as happens in prior art spectrometers. This additional information enables the analyzer to determine the properties of the sample at a generally faster rate than that of prior art spectrometers.

In some embodiments, the system includes a collimator, such as a nested set of parabolic surfaces or an array of bent capillary tubes. Preferably, each of the parabolic surfaces has a common focal point, and the focal point coincides with the desired point on the sample where the electron beam is directed, and each of the parabolic surfaces receives x-rays within a given range of takeoff angles. The collimator redirects the cone of x-rays emitted from the desired spot on the sample into a substantially parallel, collimated beam of x-rays. The collimated beam is deflected by a flat diffractor that only deflects x-rays within a desired wavelength range. The flat diffractor is oriented such that the angle between the collimated beam and the diffractor is substantially equal to the Bragg angle for the desired wavelength range. The deflected x-rays leaving the diffractor are still collimated, and directed toward the detector. The takeoff angles of the x-rays are changed when the x-rays are diffracted, but the position of each x-ray in the collimated beam is determined at least in part by its original takeoff angle, and the information is preserved through the deflection process.

In some embodiments the diffractor is a crystal, multilayer, or grating diffractor curved into a partially cylindrical shape. The axis of the cylinder lies in a plane that is substantially horizontal, and the x-rays are deflected towards the detector in a primarily vertical plane. The curved diffractor focuses the x-rays toward a focal region that is small in at least one direction, but as the x-rays emerge from the focal region, their positions are spatially separated in a manner that is dependent at least in part on the takeoff angle. A position sensitive detector records the positions of the x-rays, and thereby senses the takeoff angles of the x-rays as well.

In yet another embodiment, a single curved diffractor is disposed with a cylinder axis in a substantially vertical plane. The x-rays are deflected primarily in a horizontal plane, and their takeoff angles are substantially preserved within the vertical plane during deflection. At the detector, the x-rays are spatially separated in the vertical direction, based at least in part on their takeoff angles, and the vertical position of impingement on the detector is a measure of their takeoff angle. In this embodiment a position sensitive detector is used to record the position of each x-ray impinging on the detector.

In another embodiment, there are two or more curved diffractors, both with cylinder axes in any direction, and both set to deflect x-rays with substantially the same wavelength range, emitted by the same element. The two diffractors are disposed so that one of the diffractors collects x-rays with an average takeoff angle that is relatively low, and the other diffractor collects x-rays with an average takeoff angle that is relatively high. Each diffractor deflects x-rays into its own dedicated detector, so that a measure can be made of the x-ray intensities emitted by the desired element at both high and low takeoff angles. In this embodiment the detectors are not necessarily position sensitive detectors, and each detector measures the x-ray intensity as averaged over a range of takeoff angles that is determined by the collection aperture of its curved diffractor.

In a further embodiment the detector assembly includes a curved diffractor and a detector which is not position sensitive. The distance between the diffractor and the sample is selected such that the diffractor is relatively close to the sample and thus receives a relatively large solid angle of x-rays. Alternately, the diffractor can be made relatively larger so as to receive a larger solid angle of x-rays. It is appreciated that a combination of making the diffractor relatively larger or placing the diffractor relatively closer to the sample could also be used to increase the solid angle of x-rays received by the diffractor. Because the diffractor receives a larger solid angle of x-rays, the energy and wavelength resolution generally decreases, and thus a relatively larger range of x-ray wavelengths are deflected off the diffractor. In this embodiment the loss of resolution is intentionally traded off so as to receive a general reduction in the measurement time that comes as a result of the larger solid angle that is collected for analysis. In this embodiment the solid angle is in the range of about ten millisteradians to about fifty millisteradians.

In yet another embodiment the detector assembly consists of a collimating assembly, a flat diffractor, and a detector, which may or may not be position sensitive. The diffractor and detector are mounted together on a common rotatable stage, so that the diffractor and detector can rotate as a unit with respect to the collimator. The x-rays from the collimator form a collimated beam with a fixed direction in space. The x-rays reflect from the diffractor into the detector. As the diffractor and detector combination rotates, the wavelength of the x-rays that reflect most efficiently changes, and the spectrum of the emitted x-rays is measured. If the detector is position sensitive, the spectrum of x-rays with different takeoff angles is measured.

In any of the embodiments given, a filter can be disposed between the sample and the x-ray detector, where the filter is adapted to substantially permit transmission of the desired x-rays while substantially prohibiting transmission of other energy and particles from the sample to the detector. In some embodiments the filter substantially prohibits transmission of backscattered electrons from the sample to the detector. In other embodiments the filter substantially prohibits transmission of x-rays with wavelengths longer than those in the desired range, thereby enhancing the selectively of the system. In some embodiments both types of filters are used simultaneously.

In various embodiments the diffractor is a flat crystal, a curved crystal, a flat multilayer diffractor, a multilayer, curved surface diffractor, a flat grating, or a curved grating. The detector may variously be a two dimensional array of detector elements, a charge coupled device containing a two dimensional array of pixels, a linear array of semiconductor detectors, a position sensitive proportional counter, or a multi wire proportional counter. Preferably, the detector also detects positions of the x-rays, and most preferably the analyzer determines the properties of the sample based at least in part on the positional differences between the x-rays, the positions of the x-rays, and a number of x-rays impinging the detector at a given x-ray position per unit time. The properties detected by the apparatus preferably include elemental composition of the sample and thickness of the sample.

According to another aspect of the invention there is described an apparatus for detecting properties of a sample. An electron beam generator produces an electron beam and directs the electron beam at a desired point on the sample. The sample thereby emits characteristic x-rays that are received and parallelized by a collimator. A diffractor receives and deflects the parallelized x-rays, and a position sensitive detector receives the deflected x-rays and generates signals that are characteristic of the received x-rays. The diffractor and the detector are mounted on a common rotatable stage that is rotatable relative to at least one of the electron beam generator, the sample, and the collimator. An analyzer receives the signals from the detector and determines the properties of the sample.

According to yet another aspect of the invention there is described an apparatus for detecting properties of a sample. An electron beam generator produces an electron beam and directs the electron beam at a desired point on the sample, which causes the sample to emit characteristic x-rays. A collimator receives and parallelizes the x-rays. A diffractor receives and deflects the parallelized x-rays, and a position sensitive detector receives the deflected x-rays and generates signals that are characteristic of the received x-rays. A filter is disposed between the sample and the detector. The filter substantially permits transmission of the x-rays while substantially prohibiting transmission of other energy and particles from the sample to the detector. An analyzer receives the signals from the detector and determines the properties of the sample.

In any of the embodiments that include a collimator, a set of Soller slits can be positioned after the collimator in the collimated beam. The Soller slits reduce unwanted x-rays that are not traveling in the collimated direction from passing on to the detector and contaminating the x-ray signal. The Soller slits thereby improve the resolution of the detector assembly and the quality of the x-ray signal.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
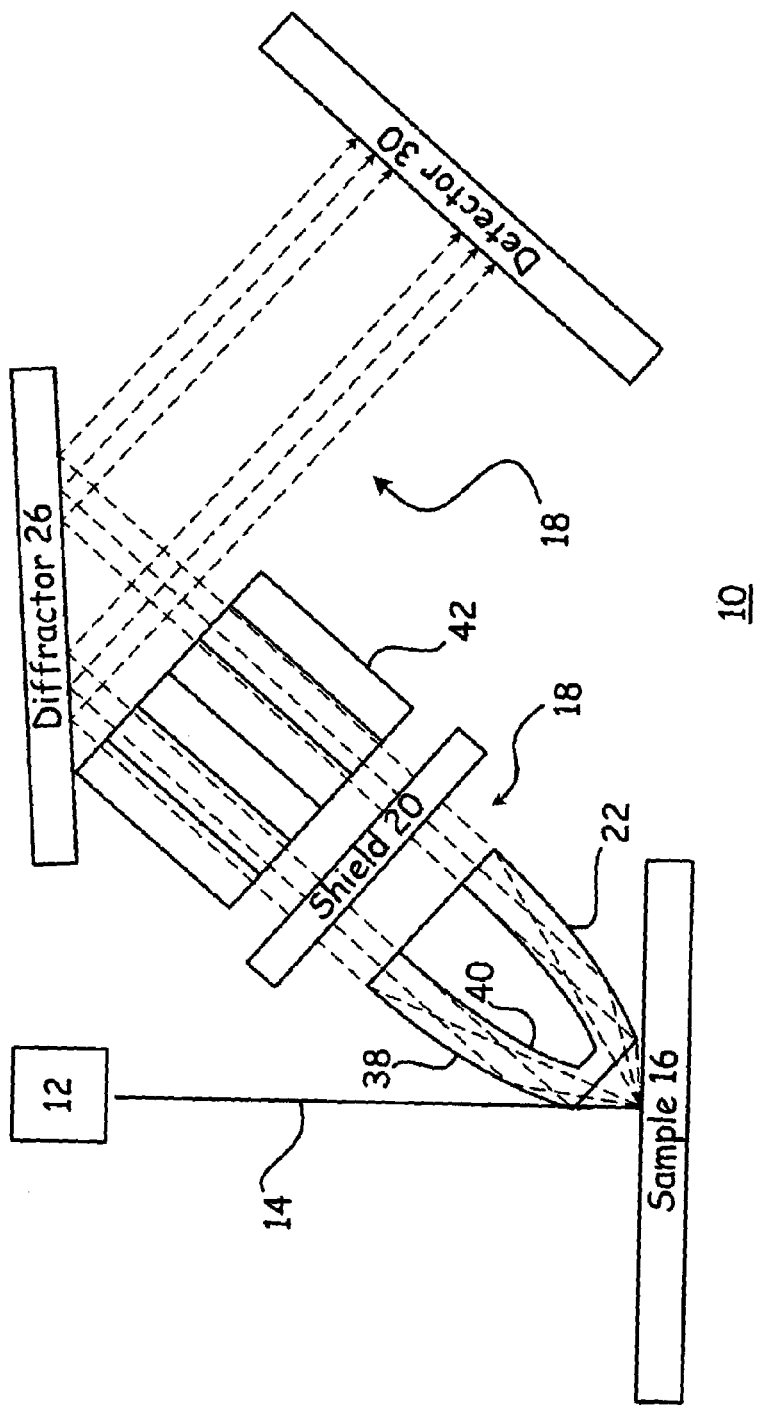
FIG. 1 is a diagrammatic representation of a system according to a first embodiment of the invention.

With reference now to FIG. 1, there is depicted a functional block diagram of an x-ray spectrometer system 10 according to a preferred embodiment of the present invention. The system 10 includes an electron beam source 12 adapted to emit an electron beam 14. The electron beam 14 impinges on a sample 16 at a desired position on the sample 16. Most preferably, the sample is an integrated circuit, such as a monolithic integrated circuit formed on a semiconducting substrate, such as that formed of a group IV material like silicon or germanium or a mixture of such, or a group III–V compound such as gallium arsenide.

As the electrons in the electron beam 14 impinge on the sample 16, x-rays 18 are emitted from the sample 16. The x-rays 18 have properties that are characteristic of the properties of the sample 16. For example, the x-rays 18 have properties that are characteristic of the thickness and elemental composition of the sample 16, which may include one or more layers on the sample 16 into which the electron beam 14 can penetrate. Different elements tend to emit x-rays 18 that have different wavelengths when they are bombarded by the electron beam 14. Thus, the wavelength of a given x-ray tends to indicate what element is present in the sample 16. If there is a greater amount of a given element in the sample 16, then there tends to be a generally higher rate of x-rays 18 emitted from the sample 16 with the wavelength that is characteristic of that element. By increasing and decreasing the energy of the electron beam 14 so that it penetrates the sample 16 to a greater or a lesser depth, a profile of the sample 16 can be produced. Thus, this information can be used to determine layer thickness and layer composition of the sample 16.

Not only are the wavelengths of the x-rays 18 characteristic of the properties of the sample 16, but the relative numbers of x-rays 18 emitted from the sample 16 at various take off angles is also characteristic of the properties of the sample 16. This is described in more detail at a later point in this discussion. The energy of the electron beam 14 is preferably controlled so as to be substantially non destructive to the sample 16, and thus the apparatus 10 can be used during fabrication of integrated circuits without damaging the integrated circuits. The sample can also be positioned so that the electron beam falls in the region between two integrated circuits. This region is known as the scribe line and is a narrow region, usually no wider than about one hundred microns, that is cut away during the last stage of integrated circuit manufacturing when the substrate is cut into individual circuits. Measurement in the scribe line also helps to prevent damage to the integrated circuits.

As mentioned above, prior art x-ray spectrometers tend to lose the takeoff angle information of the x-rays that are collected within a solid angle. However, the number of x-rays 18 within a given takeoff angle tends to include information in regard to the properties of the sample 16, and thus it is preferred that this information not be lost.

Specifically, x-rays 18 that are emitted from a buried layer within the sample 16 travel through overlying layers of material to escape the sample 16. The x-rays emitted from a given element within the buried layer have a common characteristic wavelength. As those x-rays escape through the overlying layers of the sample 16, some tend to get absorbed by the overlying layers. The number of x-rays 18 that get absorbed as they escape the sample 16 is a function of several parameters, including the composition of the overlying material, the thickness of the overlying material, and the take off angle at which the x-rays 18 escape the sample 16.

For example, if it is detected that x-rays 18 of a given wavelength have very little difference in intensity, or number of x-rays per unit time, from one take off angle to another, then that is an indication that those x-rays 18 were emitted from a material that is relatively nearer the surface of the sample 16. On the other hand, if it is detected that x-rays 18 of a given wavelength have a more significant difference in intensity from one take off angle to another, then that is an indication that those x-rays 18 were emitted from a material that is relatively deeper within the sample 16. Thus, by preserving the information in regard to the take off angle of the x-rays 18, more information in regard to the sample 16 can be collected.

Some of the preferred embodiments of the present invention preserve the information in regard to the take off angles of the x-rays 18. This is most preferably accomplished using at least one of two different methods. The first method is to use a collimator 22 as depicted in FIG. 1, and the second method is to use a curved diffractor 26 as depicted in other figures. Each of these two methods additionally relies on a position sensitive detector, and are described in more detail below. The emitted x-rays 18 in the first embodiment pass through a collimator 22 which produces parallelized x-rays 18. The collimator 22 preferably parallelizes the x-rays 18 in a manner such that the information about the takeoff angles of the x-rays 18 is preserved. However, the takeoff angle itself of each x-ray 18 is definitely lost as it passes through the collimator 22, because the collimator 22 preferably places all of the x-rays 18 in a spaced relationship along a common angular path, as depicted in FIG. 1.

In the present invention, the collimator 22 preferably encodes the takeoff angle of each x-ray 18 by providing each x-ray 18 with a positional component that is dependent at least in part upon the takeoff angle of the x-ray 18 as it enters the collimator 22. Thus, x-rays 18 with different takeoff angles preferably have different positional characteristics after passing through the collimator 22, where the positional characteristics of the x-rays 18 are at least partially dependent on the takeoff angle of the x-rays 18 as they entered the collimator 22. As depicted in FIG. 1, the emitted x-rays 18 emit from the sample 16 at different angles, and are caught by the collimator 22. The collimator 22 produces x-rays 18 that are parallelized, but which have positional differences that are dependent at least in part on the difference in the takeoff angle with which they entered the collimator 22.

The collimator 22 preferably achieves this encoding of the takeoff angles with the use of one or more parabolic surfaces 38 and 40, which parabolic surfaces 38 and 40 are preferably spaced and nested one inside another. As can be seen, those x-rays 18 which enter the collimator 22 at a takeoff angle that is relatively more parallel to the plane of the sample 16 tend to be positioned relatively lower in the parallelized column of x-rays 18 that exits the collimator 22. Similarly, those x-rays 18 which enter the collimator 22 at a takeoff angle that is relatively more perpendicular to the plan of the sample 16 tend to be positioned relatively higher in the parallelized column of x-rays 18 that exits the collimator 22. Thus, the collimator 22 preferably encodes the takeoff angles of the x-rays 18 as positional differences between the x-rays 18. One such collimator 22 is described, for example, in U.S. Pat. No. 5,682,415, the disclosure of which in regard to the parabolic surfaces and collimation of the x-rays therewith is incorporated by reference as if fully set forth herein.

It is appreciated that the number of parabolic surfaces 38 and 40 as depicted in FIG. 1 is representational only, and that in actual use the collimator 22 may have only one parabolic surface 38 or may have a large number of parabolic surfaces 38. Thus, the present invention is not to be limited to the exact number of parabolic surfaces 38 and 40 as depicted in FIG. 1. Soller slits 42 may also be used to further parallelize the x-rays 18 in various embodiments.

Figure 2:
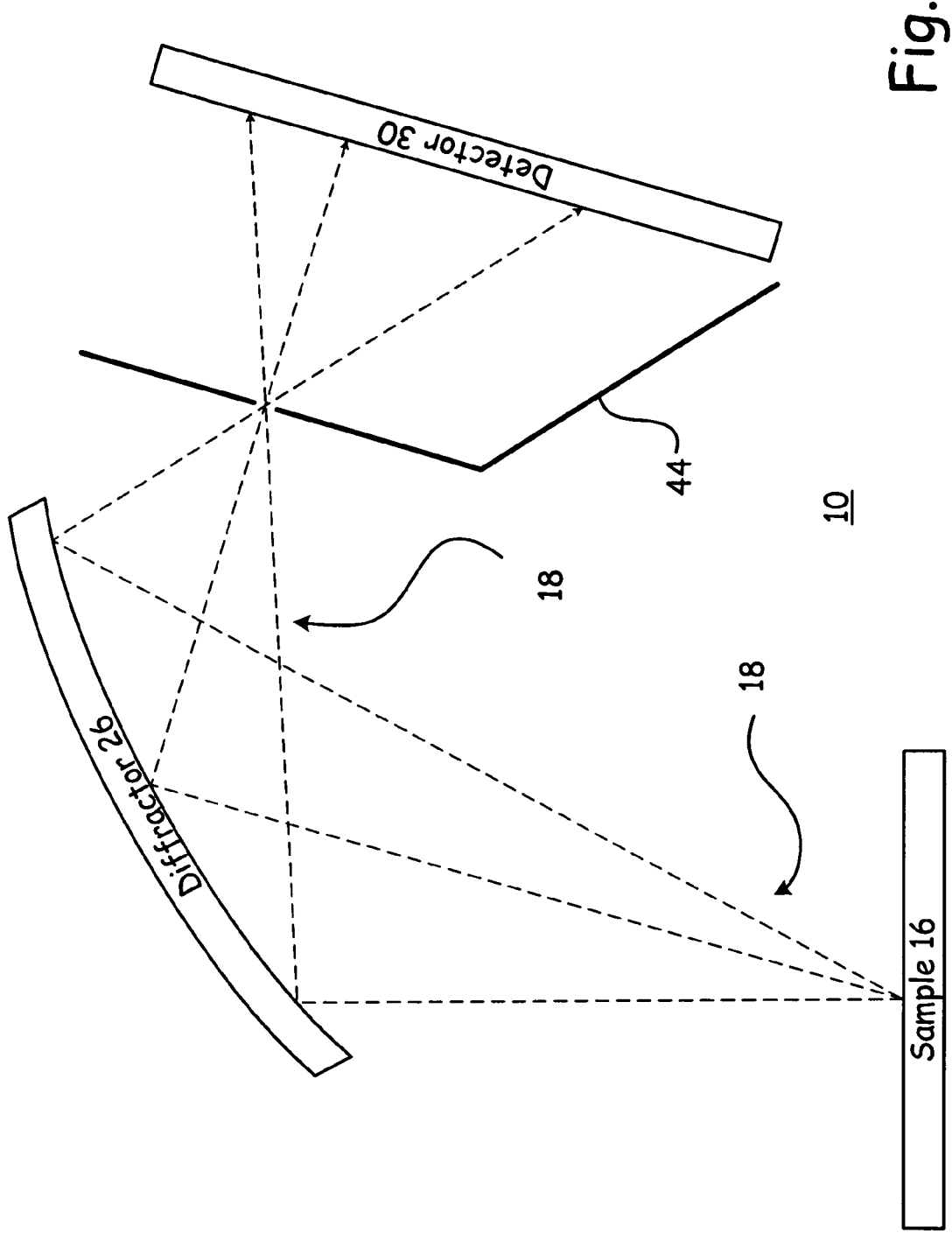
FIG. 2 is a diagrammatic representation of a collimator within a system according to a second embodiment of the invention.

Another embodiment of the invention is depicted in FIG. 2. The electron beam 14 (not depicted) creates x-rays 18 that emit from the sample 16. A fraction of the x-rays 18 are intercepted by a curved diffractor 26. The diffractor 26 is preferably curved in a cylindrical shape, with the cylinder axis disposed primarily in what is designated as a horizontal plane in the embodiment as depicted in FIG. 2. X-rays 18 within a narrow range of wavelengths are deflected from the diffractor 26 and directed into a focal region that is small in at least one dimension. An aperture 44 is used to block unwanted x-rays that are not focused at the focal region from passing through to the detector 30. The aperture 44 is preferably a thin plate of x-ray absorbing material with a hole disposed at the small focal region.

The x-ray absorbing material is preferably one or more of a variety of different materials, including stainless steel, tungsten, tantalum, or any other convenient x-ray absorbing material known in the art. The detector 30 of this embodiment is preferably a position sensitive detector 30 which records the position of each x-ray 18 that impinges upon it. The position at which an x-ray 18 impinges upon the detector 30 is determined at least in part by the takeoff angle of the x-ray 18 from the sample 16, and therefore the takeoff angle is also recorded. The information in regard to the distribution of takeoff angles is preferably used to determine the structure and composition of the sample 16 as described above.

Alternately, a detector 30 that does not have position sensitivity is used instead of a position sensitive detector 30. The takeoff angle information is lost in such an embodiment, but an advantage is gained by designing the diffractor 26 to accept a relatively large solid angle of x-rays 18. The size of the solid angle or conical section of x-rays 18 that is captured for analysis by the system 10 tends to impact various operating characteristics of the system 10. It is desirable to collect a relatively large solid angle so as to attain a higher signal to noise ratio within a shorter length of time. However, when a wider solid angle is captured, or in other words when a greater range of takeoff angles is captured for analysis, the wavelength resolution, and hence the energy resolution of the system is generally reduced. A wider range of wavelengths is deflected into the focal region and passes through the aperture. Thus, the resolution of the system 10 tends to be generally reduced when a wider solid angle of x-rays 18 is captured. Conversely, the resolution of the system 10 tends to be generally enhanced when a narrower solid angle of x-rays 18 is captured. In the application of the electron microprobe technique to measurements on semiconductors, the speed at which the measurements can be taken is generally more important than the resolution of the measurement, and thus some amount of wavelength resolution can be sacrificed without seriously degrading the measurement process.

When a wider solid angle is captured, more information per unit time is collected by the system 10, and thus the system 10 is able to take readings at a faster rate, which increases the throughput of the system 10. However, this increase in reading speed comes at the cost of a decrease in resolution. When a narrower solid angle is captured, less information per unit time is collected by the system 10, and thus the system 10 takes readings at a slower rate, which decreases the throughput of the system 10. However, this decrease in reading speed is offset with an increase in resolution.

Prior art systems tend to be designed for relatively higher resolution, even though this means they run relatively slowly. The preferred embodiments of the present system, by contrast, are designed for relatively lower resolution so that they will run faster and thus be useful as in-process inspection tools. Thus, in the preferred embodiments of the system 10 according to the present invention, a solid angle of from about ten millisteradians to about fifty millisteradians is captured for analysis, which is much greater than prior art systems.

In the present system 10, the size of the solid angle captured for analysis is preferably determined either by the proximity of the diffractor 26 to the sample or the size of diffractor 26, or a combination of the two. The x-rays 18 are preferably received and deflected by a diffractor 26. The diffractor 26 may have either a flat surface or a curved surface, and the surface of the diffractor 26 may be curved in one axis or two axes. In one embodiment, the diffractor 26 includes a plurality of diffractive layers, or in other words is a multilayer diffractor. The diffractor 26 may be made of alternating layers of tungsten and carbon, or more preferably of crystalline materials such as lithium fluoride. The deflected x-rays 18 tend to diffract off of the diffractor 26 at angles which are dependent upon the incident angle of the x-rays 18. The diffraction angle of the diffractor 26 relative to the x-rays 18 tends to preferentially select different wavelengths of the x-rays 18 for analysis, as previously described.

When a collimator 22 is used, the diffractor 26 preferably has a flat surface as depicted in FIG. 1. Although the angle of x-ray 18 diffraction off of a flat diffractor 26 tends to change the positional differences between parallelized x-rays 18, the positional differences tend to be uniformly changed, or otherwise changed in a manner where the takeoff angle encoded in the positional differences can be preserved.

Figure 3:
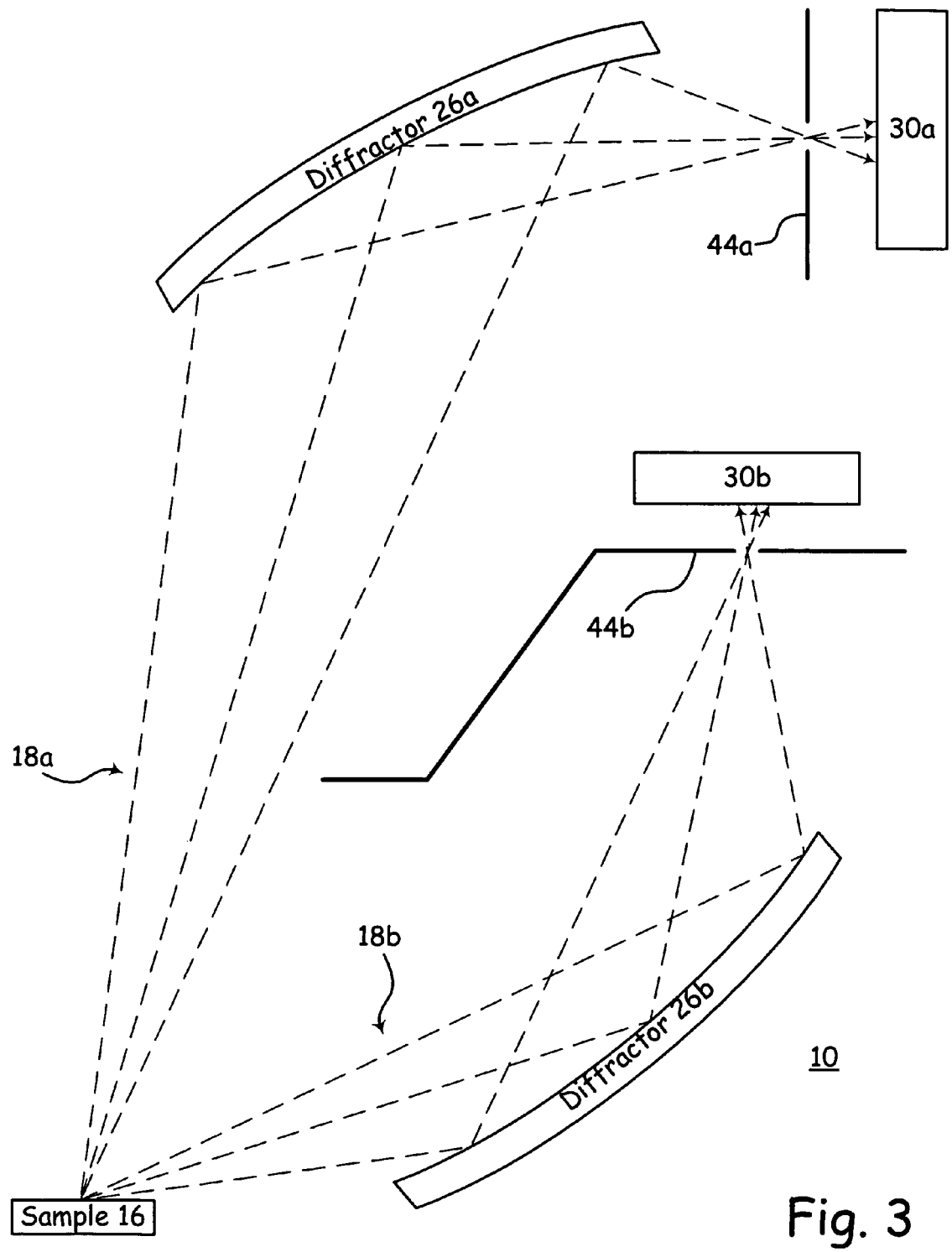
FIG. 3 is a diagrammatic representation of a curved diffractor within a system according to a third embodiment of the invention.

Another embodiment of the invention is depicted in FIG. 3. X-rays 18b having a substantially low takeoff angle are intercepted by a curved diffractor 26b and directed into a focal region. An aperture 44b at the focal region allows the desired x-rays 18b to pass to the detector 30b. Detector 30b is preferably not position sensitive in this embodiment. A second set of x-rays 18a that have a higher average takeoff angle than x-rays 18b are intercepted by a curved diffractor 26a, and deflected into a second focal region. Aperture 44a allows the desired x-rays 18a from diffractor 26a to pass to the second detector 30a. Detector 30a is preferably also not a position sensitive detector in this embodiment. In this way, x-ray intensity information is recorded at two average take-off angles, and is used to aid in determining the structure of sample 16. This embodiment has the advantage over other embodiments in that the difference in takeoff angle between x-ray sets 18a and 18b can be made larger than the takeoff angle range that can be measured in the other embodiments. This embodiment also eliminates the expense and complexity of a position sensitive detector.

Figure 4:
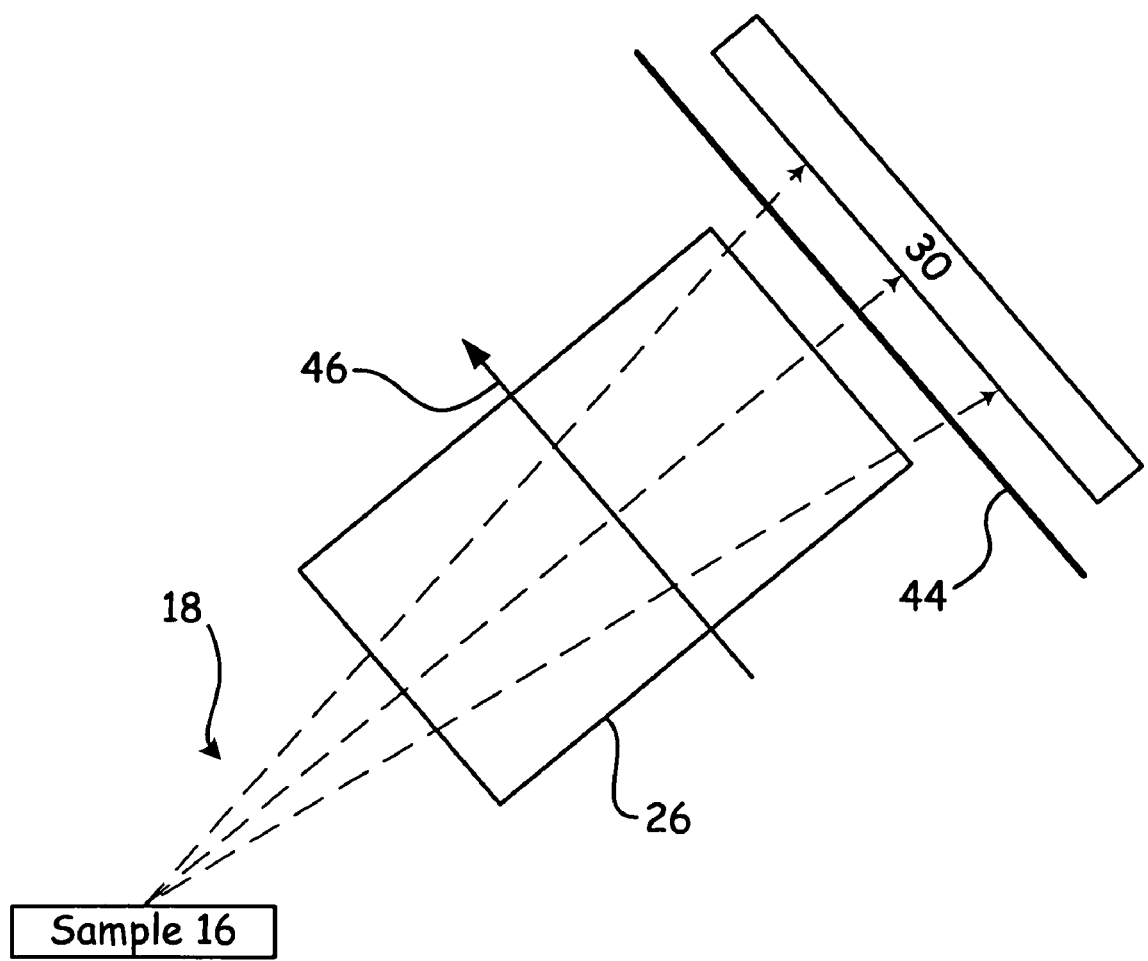
FIG. 4 is a diagrammatic representation of a curved diffractor within a system according to a fourth embodiment of the invention.

Yet another embodiment of the invention is depicted in FIG. 4. X-rays 18 emitted by the sample 16 are deflected by a diffractor 26. The diffractor is curved in a cylindrical shape with the cylinder axis 46 lying in a substantially vertical plane, generally relative to the path of the x-rays 18. The x-rays 18 are deflected into a focal region that is small in at least one dimension and an aperture 44 allows only the focused x-rays to pass on to the position sensitive detector 30. The x-rays 18 are deflected out of the plane of the paper on which FIG. 4 is drawn, and so the deflection is not seen in FIG. 4. Similarly, the focal region and the aperture 44 also lie in a substantially vertical plane, and so they too are not easily seen in the figure. The takeoff angle information is preserved in the positions at which the x-rays impinge upon the detector.

Figure 5:
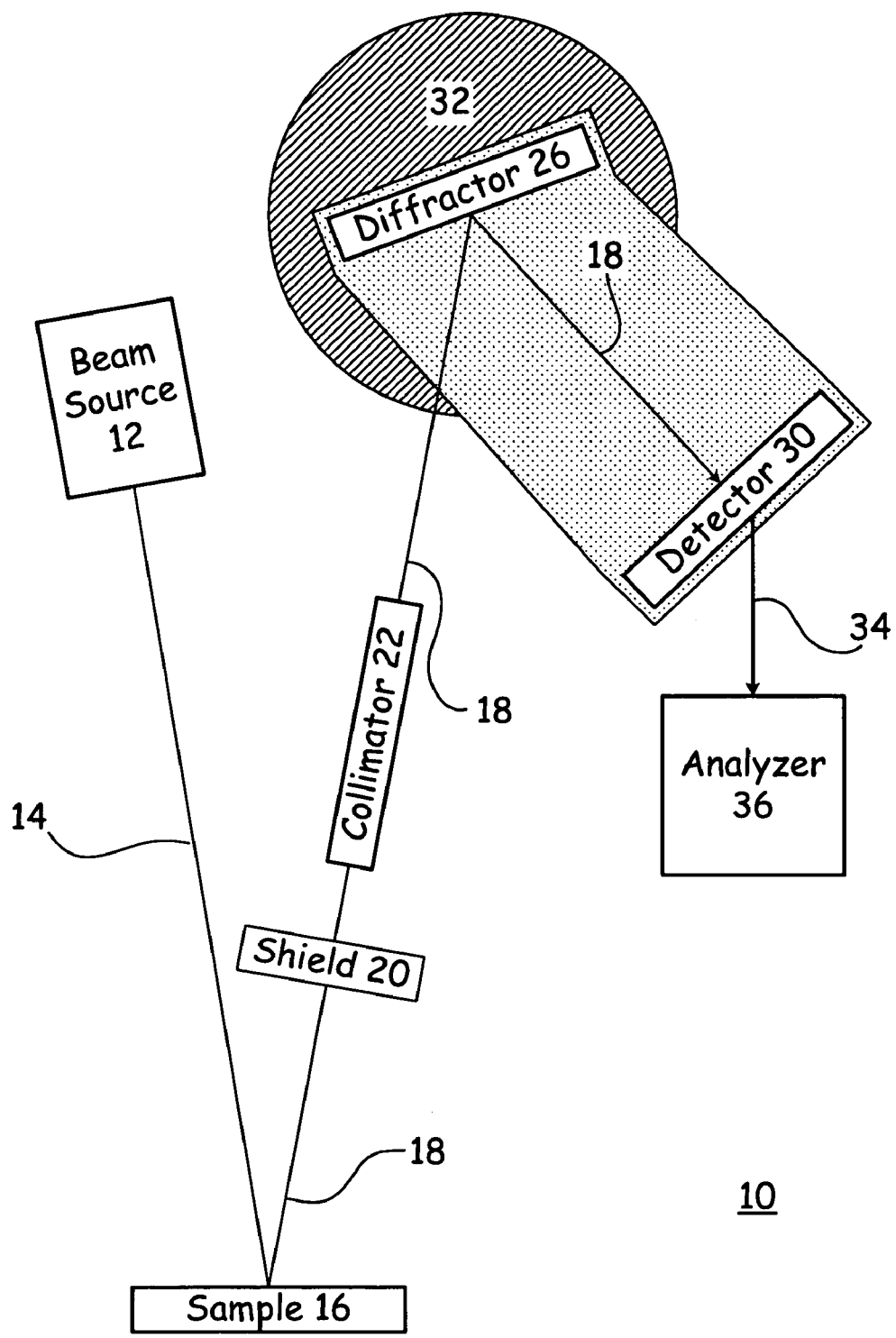
FIG. 5 is a diagrammatic representation of a system according to a fifth embodiment of the invention.

A further embodiment is depicted in FIG. 5. The electron beam source 12 produces an electron beam 14 which creates x-rays from the sample 16. The x-rays 18 emitted from the sample 16 preferably pass through a shield 20 that is designed to substantially pass the emitted x-rays 18 and to substantially block anything else, such as energy or particles. Most preferably, the shield 20 substantially blocks backscattered electrons from the electron beam 14 and low energy x-rays. By shielding the passage of other things besides the desired x-rays 18, the system 10 tends to reduce false readings and other problems.

The shield 20 is preferably a piece of physical material and not merely an electrical field, such as an E field or a B field, that uses electromotive forces to prohibit electrons from passing, and which would tend to allow a greater number of electrons or other energy or particles to pass than a physical shield. The shield 20 is preferably constructed of a thin layer of material of sufficient thickness to prohibit undesired energy and particles from passing, while simultaneously allowing a significant portion of the x-rays 18 to pass. A particularly preferred material for the shield 20 is beryllium. However, other materials, such as polyimide, lithium, aluminum, and the like may also be used for the shield 20.

For example, a beryllium shield with a thickness of about fifty microns is sufficient to screen substantially all backscattered electrons with an energy of about twenty thousand electron volts, such as may be produced by bombarding a copper sample 16 with a twenty thousand electron volt electron beam. The characteristic energy of the copper x-rays emitted in such a configuration is only about eight thousand electron volts. However, the beryllium shield, which stops essentially all of the back scattered electrons from passing, will allow to pass about ninety-nine percent of the characteristic x-rays emitted from the copper sample 16.

The x-rays 18 are collected by a collimator 22 and formed into a collimated beam. The collimated x-rays 18 are then deflected by a flat diffractor 26 onto a detector 30. The diffractor 26 is preferably mounted on a rotatable stage 32, such that the diffractor 26 can be rotated relative to the x-rays 18 that are entering the diffractor 26. By changing the angle of the diffractor 26 relative to the x-rays 18, the diffraction properties of the diffractor 26 cause x-rays 18 having different wavelengths to be deflected differently, as previously mentioned. Thus, by changing the angle of the diffractor 26 relative to the x-rays 18, the system 10 can more specifically select a given wavelength range of interest for analysis. The rotatable stage 32 is described in more detail hereafter.

The diffracted x-rays 18 are preferably received with a detector 30, which is most preferably a position sensitive detector, which detects where on the detector 30 each impinging x-ray 18 lands. By using a detector 30 that can determine the positions at which the x-rays 18 are received, the takeoff angles of the x-rays 18 can be determined. This position sensitive information can be alternately gathered in either one dimension or in two dimensions by the detector 30. Thus, the detector 30 is able to relay information in regard to the takeoff angle of each x-ray 18 that is received, by providing the positional information of the received x-ray 18 on the detector 30. As introduced above, this additional takeoff angle information enables the system 10 to make faster readings and also provides confirmatory data for the readings that are taken.

The position sensitive detector 30 is most preferably an array of charge coupled devices. In alternate embodiments the detector 30 is a linear array of semiconductor devices, a position sensitive proportional counter, or a multi-wire proportional counter. In one embodiment, the position sensitive detector is a two dimensional array of pixels oriented horizontally in rows and vertically in columns. In such embodiments, the takeoff angle is determined by the pixel row and column in which the x-ray 18 is detected. The detector 30 may also be an array of energy dispersive x-ray detectors that provides simultaneous angular and energy resolved detection of the diffracted x-rays 18.

In one embodiment, the collection surface of the position sensitive detector 30 is subdivided or binned in some manner, such that the x-rays 18 which impinge within a given binned area of the detector 30 are aggregated together in the signal 34 that is delivered to the analyzer 36. For example, the surface of the detector 30 could be either physically or logically divided into a number of bins of from about five bins to about twenty bins. As suggested above, this division can either be physical in the detector 30, or logical in either or both of the detector 30 and the analyzer 36. In this manner, x-rays 18 which have slightly different takeoff angles can be grouped together by either the detector 30 or the analyzer 36 as being indicative of similar properties of the sample 16. Thus, computational time within the analyzer 36 can be reduced, because each tiny positional difference is not analyzed as an individual occurrence. However, in other embodiments, each x-ray 18 that impinges on the detector 30 is analyzed separately.

The information determined by the detector 30 is preferably provided as signals 34 to an analyzer 36. The analyzer 36 uses a host of information to determine the properties of the sample 16, some of which information is well known in the art. However, some information used by the analyzer 36 is novel to the present invention. The analyzer 36 preferably uses information such as, or which is dependent on, the energy level of the electron beam 14, the breadth of the solid angle of emitted x-rays 18 collected by the diffractor 26, the diffraction angle of the diffractor 26, the positional differences in the x-rays 18, such as may be provided by the collimator 22 and the impingement positions of the x-rays 18 on the detector 30, and the rate of impingement of the x-rays 18 on the detector 30 over a given length of time.

In one embodiment, the takeoff angles of the x-rays 18 as emitted from the sample 16 are binned into solid angles $\theta_1$, $\theta_2, \ldots \theta_n$, where n ranges from about five to about twenty. In this embodiment, data for each property of the sample 16 being measured consists of an array of values, one value for each angular bin, where each bin has an associated intensity value.

The system 10 is preferably configured for selectively measuring the spectra around a desired elemental peak position, such as for light elements like nitrogen, oxygen or boron. In a conventional system with these capabilities, the detector is mounted on a separate rotational stage from the diffractor, so that the detector and the diffractor each rotate at different rates. In a typical prior art system, the detector rotates at twice the angular rotation rate of the diffractor, and intercepts the deflected x-rays at the same point on the detector face throughout a desired rotational range of the diffractor. Because prior art detectors are not position sensitive, this characteristic of having the x-rays arrive at the detector at the same position on the detector is very important. However, it is fairly difficult to maintain the relative alignment between the diffractor and the detector in such a system. Such a system typically requires either two separate drive mechanisms or a cam and follower system.

However, when using the system 10 according to the present invention, the diffractor 26 and the detector 30 are preferably mounted together on a common rotational stage 32, as depicted in FIG. 5. Thus, when either the diffractor 26 or the detector 30 are rotated by the stage 32 relative to any of the other elements of the system 10, and most notably the x-rays 18, the other one of the two is rotated also. The stage 32 is constructed such that the deflection angle of the diffracted x-rays 18 changes at twice the rate of change of the angle of the diffractor 26. Thus, the detector 30 is preferably configured with a sufficiently large receiving surface to receive the x-rays 18 as the change in scanning angle sweeps the x-rays 18 across the surface of the detector 30. As the detector 30 is already preferably an array of sufficient size to detect positional differences between the x-rays 18, this is not an additional burden on the construction of the system 10, and the total scan range of the system 10 is preferably limited only by the size of the receiving face or sensor array portion of the detector 30.

The rotational stage 32 preferably has an angular range and resolution sufficient to satisfy the energy range and energy scan resolution required for analyzing nitrogen, such as in a tantalum nitride layer as used in a copper interconnect of an integrated circuit. The total angular rotation of the rotational stage 32 is preferably determined by the low energy diffraction angle minus the high energy diffraction angle for the materials being analyzed. When the material is nitrogen, for example, the total rotation of the rotational stage 32 is about 26.9 degrees minus about 20.5 degrees, yielding a desired rotation of about 6.4 degrees. The desired angular resolution, assuming a needed energy resolution of about one half of an electron volt, is preferably the difference in the diffraction angle of the high energy limit minus the one half of an electron volt, and the diffraction angle of the high energy limit. The high energy limit is preferably used, because the angular rate of change tends to be much smaller at the higher energy end of the scan range. Using nitrogen as an example, the desired resolution is about 20.531 degrees minus about 20.507 degrees, which yields about 0.024 degrees.

The rotational stage 32 is preferably automated and not limited as to the type of actuator that drives the stage 32, provided that the actuation device is preferably compatible with the rest of the system 10 and the analysis being performed. The rotational stage 32 preferably includes limit devices that indicate low and high angles of travel of the rotational stage 32, and also preferably indicate a home position for the rotational stage 32. The limit devices preferably prevent the stage 32 from rotating too far and damaging one or more elements of the system 10. In the embodiments which include the rotational stage 32, substantially all of the mechanical elements of the analyzer 10 are aligned with respect to the rotational stage 32, and the rotational stage 32 is preferably disposed inside of a vacuum chamber.

The detector 30 preferably includes a rectangular receiving surface that is tall enough to collect the output of the deflected x-rays 18 and wide enough to collect an entire scan range of the diffractor 26. The preferred minimum height of the detector 30 is the diameter of the x-rays 18 plus a safety margin, preferably of about ten percent. For a typical system 10, the height of the detector 30 is preferably about twenty-two millimeters.

The width of the detector 30 is preferably determined by considering the scan range of the diffractor 26, and how it effects the travel of the x-rays 18 across the surface of the detector 30. For example, if the detector 30 is fixed at the nominal diffraction angle $\theta$ relative to the detector 30, the deviation of the x-rays 18 at the limit of the scan $\theta_B$ is defined as the absolute value of the difference in angle for the range $|\theta-\theta_B|$. The linear displacement of an outer edge of the diffracted beam 18 is given by $L \tan(|\theta-\theta_B|)+d/2$, where L is the distance from the diffractor 26 to the detector 30 and d is the diameter of the x-ray bundle 18. The total required detector 30 width W, is preferably given by $W=L (\tan|\theta-\theta_{HE}|+\tan|\theta-\theta_{LE}|)+d$, where $\theta_{LE}$ is the low energy diffraction angle and $\theta_{HE}$ is the high energy diffraction angle.

To continue the nitrogen example given above, the nominal diffraction angle $\theta$ is 23.26 degrees, the high energy diffraction angle $\theta_{HE}$ is 20.51 degrees, and the low energy diffraction angle $\theta_{LE}$ is 26.91 degrees. For L equal to fifty millimeters and d equal to twenty millimeters, the width W is about 25.6 millimeters. In the case where the detector 30 width W is fixed at some size, say for example 30.2 millimeters, it is useful to determine the maximum distance L between the diffractor 26 and the detector 30. Solving the foregoing equations backwards yields an L that is equal to about 91.2 millimeters.

Since the diffractor 26 and detector 30 are preferably mounted on a common rotation stage 32, the use of separate drive mechanisms for the diffractor 26 and detector 30 is avoided. Hence, the system 10 is substantially more stable than prior art systems, in that it is easier to maintain the diffracted x-rays 18 in an aligned relationship with the detector 30. Using a single rotational stage 32 reduces the cost of the system 10, and at the same time increases the stability of the system 10. Also, because the distance L of the detector 30 from the diffractor 26 is preferably not critical, as described above, there is no requirement to adjust the distance L. If the detector 30 is of sufficient height, then there are no related, special requirements on the position of the detector 30 in the longitudinal direction.

Without limiting the invention, the following example of the method of use of an x-ray system 10 according to the present invention is provided below.

A sample 16 is loaded into the system 10, where the sample 16 includes a one thousand angstrom thick copper layer overlying a one hundred angstrom thick tantalum nitride layer disposed on a silicon substrate. Accordingly, there are three variables of interest, which are the thickness of the tantalum nitride layer, the nitrogen concentration of the tantalum nitride layer, and the thickness of the copper layer. A conventional system without the angle resolved detection of the present system 10 generates only three data values, which are the copper x-ray counts, the tantalum x-ray counts, and the nitrogen x-ray counts. With so little data, it is generally quite difficult to distinguish variations in the nitrogen concentration of the tantalum nitride layer from thickness variations in the copper layer, because the copper layer tends to absorb the nitrogen x-rays as they are emitted from the tantalum nitride layer. Thus, the data tends to be confounded between at least two possible causes of variation.

Using the angle resolved detection system 10 of the present invention, the nitrogen x-ray absorption produces an angle dependent intensity. Nitrogen x-rays with higher takeoff angles, or in other words with takeoff angles that are closer to perpendicular to the sample 16 surface, will tend to be more intense because the nitrogen x-rays have traveled through less of the copper layer thickness as they escaped the sample 16. This angular variation in x-ray intensity provides additional information in regard to both the thickness of the copper layer and the concentration of the nitrogen in the tantalum nitride layer. The parabolic collimator 22 is preferably adapted to work best for low energy x-rays like nitrogen, and a 12 degree range of collected takeoff angles is enough to detect a significant variation in x-ray intensity with takeoff angle.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for detecting properties of a sample, the apparatus comprising:
    an electron beam generator adapted to produce an electron beam and direct the electron beam at a desired point on the sample, the sample thereby emitting characteristic x-rays at takeoff angles,
    a diffractor adapted to receive and deflect the x-rays,
    means for preserving, at least in part, information indicative of the takeoff angles of the x-rays,
    a position sensitive detector adapted to receive the deflected x-rays and detect the information indicative of the takeoff angles of the x-rays and generate signals that are characteristic of the received x-rays, and
    an analyzer adapted to receive the signals from the detector and determine the properties of the sample based at least in part on the information indicative of the takeoff angles of the x-rays.

2. The apparatus of claim 1, wherein the means for preserving the information indicative of the takeoff angles of the x-rays comprises the diffractor having a cylindrically curved surface with an axis of curvature in a substantially horizontal plane, the diffractor adapted to receive the x-rays in a substantially vertical plane, and thereby deflect the x-rays along a substantially vertical plane, at angles that are dependent at least in part on the takeoff angles of the x-rays.

3. The apparatus of claim 1, wherein the means for preserving the information indicative of the takeoff angles of the x-rays comprises:
    a collimator adapted to receive and parallelize the x-rays and convert the takeoff angles of the x-rays to positional differences between the parallelized x-rays,
    the diffractor having a flat surface to preserve at least in part the positional differences between the parallelized x-rays as they are deflected, and
    the detector adapted to sense in at least one dimension and report the positional differences between the parallelized x-rays.

4. The apparatus of claim 3, wherein the collimator includes a plurality of spaced and nested parabolic surfaces, where each of the parabolic surfaces has a common focal point, and the focal point coincides with the desired point on the sample where the electron beam is directed, and each of the parabolic surfaces receives x-rays within a given range of takeoff angles.

5. The apparatus of claim 1, further comprising a filter disposed between the sample and the detector, the filter adapted to substantially permit transmission of the x-rays while substantially prohibiting transmission of at least one of other energy, particles, and backscattered electrons from the sample to the detector.

6. The apparatus of claim 1, wherein the diffractor is one of a crystalline flat surface diffractor, a multilayer flat surface diffractor, a crystalline curved surface diffractor, a multilayer curved surface diffractor, a flat grating, and a curved grating.

7. The apparatus of claim 1, wherein the detector consists of at least one of a two dimensional array of detector elements, a charge coupled device containing a two dimensional array of pixels, a linear array of semiconductor detectors, a position sensitive proportional counter, and a multi-wire proportional counter.

8. The apparatus of claim 1, wherein the detector also detects positions of the x-rays, and the analyzer determines the properties of the sample based at least in part on the positional differences between the x-rays, the positions of the x-rays, and a number of x-rays impinging the detector at a given x-ray position per unit time.

9. The apparatus of claim 1, wherein the properties detected by the apparatus include elemental composition of the sample and thickness of the sample.

10. An apparatus for detecting properties of a sample, the apparatus comprising:
    an electron beam generator adapted to produce an electron beam and direct the electron beam at a desired point on the sample, the sample thereby emitting characteristic x-rays,
    a collimator adapted to receive and parallelize the x-rays and convert the takeoff angles of the x-rays to positional differences between the parallelized x-rays,
    a diffractor having a flat surface and adapted to receive and deflect the x-rays, while preserving, at least in part, the positional differences between the x-rays, a detector adapted to receive the x-rays from the diffractor and generate signals that are characteristic of the received x-rays, where the diffractor and the detector are mounted in a fixed relationship on a common rotatable stage that is rotatable relative to at least one of the electron beam generator, the sample, and the collimator, and an analyzer adapted to receive the signals from the detector and determine the properties of the sample based at least in part on the positional differences between the x-rays.

11. The apparatus of claim 10, further comprising a filter disposed between the sample and the detector, the filter adapted to substantially permit transmission of the x-rays while substantially prohibiting transmission of at least one of other energy, particles, and backscattered electrons from the sample to the detector.

12. The apparatus of claim 10, wherein the collimator includes a plurality of spaced and nested parabolic surfaces, where each of the parabolic surfaces has a common focal point, and the focal point coincides with the desired point on the sample where the electron beam is directed, and each of the parabolic surfaces receives x-rays within a given range of takeoff angles.

13. The apparatus of claim 10, wherein the detector is a position sensitive detector consisting of at least one of a two dimensional array detector elements, a charge coupled device containing a two dimensional array of pixels, a position sensitive proportional counter, and a multi-wire proportional counter, and the detector also detects positions of the x-rays, and the analyzer determines the properties of the sample based at least in part on the positional differences between the x-rays, the positions of the x-rays, and a number of x-rays impinging the detector at a given x-ray position per unit time.

14. The apparatus of claim 10, wherein the properties detected by the apparatus include elemental composition of the sample and thickness of the sample.

15. An apparatus for detecting properties of a sample, the apparatus comprising:
an electron beam generator adapted to produce an electron beam and direct the electron beam at a desired point on the sample, the sample thereby emitting characteristic x-rays at takeoff angles, a first curved surface diffractor adapted to receive and deflect the x-rays that are received at low takeoff angles, a second curved surface diffractor adapted to receive and deflect the x-rays that are received at high takeoff angles, a first detector adapted to receive the x-rays from the first diffractor, and generate signals that are characteristic of the received x-rays, a second detector adapted to receive the x-rays from the second diffractor, and generate signals that are characteristic of the received x-rays, and an analyzer adapted to receive the signals from the first detector and the second detector and determine the properties of the sample, based at least in part on differences between the signals received from the first detector and the second detector.

16. The apparatus of claim 15, further comprising a filter disposed between the sample and the first and second detectors, the filter adapted to substantially permit transmission of the x-rays while substantially prohibiting transmission of at least one of other energy, particles, and backscattered electrons from the sample to the first and second detectors.

17. The apparatus of claim 15, wherein the first and second detectors are position sensitive detectors each consisting of at least one of a two dimensional array of detector elements, a charge coupled device containing a two dimensional array of pixels, a linear array of semiconductor detectors, a position sensitive proportional counter, and a multi-wire proportional counter, and the detectors also detects positions of the x-rays, and the analyzer determines the properties of the sample based at least in part on the positional differences between the x-rays, the positions of the x-rays, and a number of x-rays impinging the detectors at a given x-ray position per unit time.

18. An apparatus for detecting properties of a sample, the apparatus comprising:
an electron beam generator adapted to produce an electron beam and direct the electron beam at a desired point on the sample, the sample thereby emitting characteristic x-rays at takeoff angles, a curved surface diffractor adapted to receive the x-rays within a desired solid angle of from about ten millisteradians to about fifty millisteradians, and deflect the x-rays, a detector adapted to receive the deflected x-rays and generate signals that are characteristic of the received x-rays, and an analyzer adapted to receive the signals from the detector and determine the properties of the sample.

19. The apparatus of claim 18, wherein the diffractor is adapted to receive the x-rays within the desired solid angle by at least one of enlarging a receiving surface area of the diffractor so as to receive the desired solid angle, and bringing the diffractor closer in proximity to the sample so as to receive the desired solid angle.

20. The apparatus of claim 18, further comprising a filter disposed between the sample and the detector, the filter adapted to substantially permit transmission of the x-rays while substantially prohibiting transmission of at least one of other energy, particles, and backscattered electrons from the sample to the detector.

* * * * *